(12) United States Patent
Kanikanti et al.

(10) Patent No.: US 7,780,986 B2
(45) Date of Patent: Aug. 24, 2010

(54) METHOD OF PREPARING SUSTAINED-RELEASE PREPARATIONS OF QUINOLONE ANTIBIOTICS

(75) Inventors: Venkata-Rangarao Kanikanti, Leverkusen (DE); Roland Rupp, Bergisch Gladbach (DE); Wolfgang Weber, Cologne (DE); Peter Deuringer, Cologne (DE); Jan-Olav Henck, Willich (DE); Heino Stab, Cologne (DE); Takaaki Nishioka, Nabari (JP); Yoshifumi Katakawa, Kusatsu (JP); Chika Taniguchi, Nishinomiya (JP); Hitoshi Ichihashi, Suita (JP)

(73) Assignee: Bayer Schering Pharma AG, Leverkusen (DE)

( * ) Notice: Subject to any disclaimer, the term of this patent is extended or adjusted under 35 U.S.C. 154(b) by 58 days.

(21) Appl. No.: 11/560,594

(22) Filed: Nov. 16, 2006

(65) Prior Publication Data

US 2007/0065509 A1     Mar. 22, 2007

Related U.S. Application Data

(62) Division of application No. 10/311,913, filed as application No. PCT/EP01/06695 on Jun. 13, 2001.

(30) Foreign Application Priority Data

Jun. 26, 2000   (DE) .............................. 100 31 043

(51) Int. Cl.
| | |
|---|---|
| A61K 9/22 | (2006.01) |
| A61K 9/20 | (2006.01) |
| A61K 9/24 | (2006.01) |
| A61K 31/47 | (2006.01) |
| A61K 31/495 | (2006.01) |
| A61K 31/496 | (2006.01) |
| A61K 47/30 | (2006.01) |
| A61K 47/38 | (2006.01) |
| A61P 31/00 | (2006.01) |
| A61P 31/04 | (2006.01) |

(52) U.S. Cl. ...................... 424/468; 424/464; 424/472; 514/252.1; 514/255.05; 514/312; 514/777; 514/781; 514/960; 514/964

(58) Field of Classification Search .................. None
See application file for complete search history.

(56) References Cited

U.S. PATENT DOCUMENTS

| | | | |
|---|---|---|---|
| 2,951,792 A | 9/1960 | Swintosky | |
| 4,122,157 A | 10/1978 | Huber | |
| 4,293,539 A | 10/1981 | Ludwig et al. | |
| 4,369,172 A | 1/1983 | Schor et al. | |
| 4,370,313 A | 1/1983 | Davies | |
| 4,440,740 A | 4/1984 | Fix et al. | |
| 4,443,428 A * | 4/1984 | Oshlack et al. ............. 424/457 |
| 4,478,822 A | 10/1984 | Haslam et al. | |
| 4,530,928 A | 7/1985 | Haslam et al. | |
| 4,639,458 A | 1/1987 | Katdare | |
| 4,708,874 A | 11/1987 | De Haan et al. | |
| 4,734,285 A | 3/1988 | Alderman | |
| 4,786,503 A | 11/1988 | Edgren et al. | |
| 4,834,965 A | 5/1989 | Martani et al. | |
| 4,839,177 A | 6/1989 | Colombo et al. | |
| 4,869,908 A | 9/1989 | Kirschner et al. | |
| 4,892,741 A | 1/1990 | Ohm et al. | |
| 5,007,790 A | 4/1991 | Shell | |
| 5,032,406 A | 7/1991 | Dansereau et al. | |
| 5,051,262 A | 9/1991 | Panoz et al. | |
| 5,085,865 A | 2/1992 | Nayak | |
| 5,188,840 A | 2/1993 | Iida et al. | |
| 5,213,808 A | 5/1993 | Bar-Shalom et al. | |
| 5,286,754 A | 2/1994 | Streuff et al. | |
| 5,422,123 A | 6/1995 | Conte et al. | |
| 5,462,747 A | 10/1995 | Radebaugh et al. | |
| 5,464,633 A | 11/1995 | Conte et al. | |
| 5,472,710 A * | 12/1995 | Klokkers-Bethke et al. . 424/468 |
| 5,549,913 A | 8/1996 | Colombo et al. | |
| 5,582,837 A | 12/1996 | Shell | |
| 5,681,583 A * | 10/1997 | Conte et al. ............... 424/472 |
| 5,695,784 A | 12/1997 | Pollinger et al. | |
| 5,705,190 A * | 1/1998 | Broad et al. ................ 424/465 |
| 5,738,874 A | 4/1998 | Conte et al. | |
| 5,780,057 A | 7/1998 | Conte et al. | |
| 5,900,425 A | 5/1999 | Kanikanti et al. | |
| 5,972,389 A | 10/1999 | Shell et al. | |
| 6,187,341 B1 * | 2/2001 | Johnson et al. ............. 424/480 |
| 6,190,692 B1 | 2/2001 | Busetti et al. | |

(Continued)

FOREIGN PATENT DOCUMENTS

DE      3142854 A1      5/1983

(Continued)

OTHER PUBLICATIONS

Foye, William O.; Lemke, Thomas L.; Williams, David A.; "Principles of Medicinal Chemistry" 1995, Lippincott Williams & Wilkins, 4th edition, p. 768-769.*

Primary Examiner—Yvonne L Eyler
Assistant Examiner—Christopher R Lea
(74) Attorney, Agent, or Firm—Banner & Witcoff, Ltd.

(57) ABSTRACT

The present invention relates to an orally administrable preparation comprising a quinolone antibiotic which releases the active compound with a delay.

12 Claims, No Drawings

U.S. PATENT DOCUMENTS

| | | |
|---|---|---|
| 6,261,601 B1 * | 7/2001 | Talwar et al. ............... 424/469 |
| 6,270,799 B1 | 8/2001 | Siefert et al. |
| 6,340,475 B2 | 1/2002 | Shell et al. |
| 6,488,962 B1 | 12/2002 | Berner et al. |
| 2003/0044466 A1 | 3/2003 | Markey et al. |
| 2003/0104062 A1 | 6/2003 | Berner et al. |

FOREIGN PATENT DOCUMENTS

| | | |
|---|---|---|
| DE | 4414544 C2 | 11/1994 |
| EP | 0111144 B1 | 12/1986 |
| EP | 0265061 A1 | 1/1992 |
| GB | 1346609 | 2/1974 |
| GB | 2203338 A | 10/1988 |
| GB | 2123291 A | 11/2006 |
| WO | 0015198 | 3/2000 |
| WO | 9915172 | 11/2006 |

* cited by examiner

METHOD OF PREPARING SUSTAINED-RELEASE PREPARATIONS OF QUINOLONE ANTIBIOTICS

This application is a division of U.S. application Ser. No. 10/311,913, filed May 30, 2003, which is the U.S. national stage of PCT/EP01/06695, filed Jun. 13, 2001. The disclosures of these applications are hereby incorporated by reference in their entireties.

The present invention relates to solid, orally administrable matrix preparations of quinolone antibiotics having delayed release and to a process for their preparation.

Active compounds from the quinolones class have been employed for a long time as broad-spectrum antibiotics, and numerous administration forms are obtainable on the market, such as tablets, infusion solutions, eye drops etc.

For many medicaments—as also for the quinolones class—formulations are desirable which after administration once daily guarantee a controlled, long-lasting and uniform release of the active compound. In this way, the desired active compound concentration in the plasma (below: "plasma level") and the therapeutic action can be maintained over a relatively long period without large variations. Formulations which release the active compound in this manner over a relatively long period are designated as delayed-release or controlled-release (CR) preparations.

It is very difficult, however, to develop orally administrable quinolone preparations which, in spite of administration only once daily, guarantee an adequately high antibiotic action; the patient must therefore take at least two doses daily. It is desirable, however, to reduce the frequency of taking of such quinolone antibiotics to once daily.

For the production of preparations having controlled release of active compound, in principle various techniques are known. Thus it is often desired to leave the preparation for a relatively long period in the stomach in order to make possible the rapid and complete absorption of the active compound to be delayed in the absorption window (i.e. in the section of the gastrointestinal tract in which absorption takes place). The residence time in the stomach, however, depends strongly on the nature and nutritive value of the food in the stomach (S. S. Davis in G. Hardy et al., Drug Delivery to the Gastrointestinal Tract, Ellis Holwood Ltd., Chichester, England 1989). In order to prolong the residence time in the stomach, various attempts have been investigated which either a) increase the density of the preparation (EP-A 265 061), b) use special additives such as ammonium myristate which, as is known, slow the further transport of preparations in the gastrointestinal tract (R. Groning; G. Heung, Int. J. Pharm. 56, 111 (1989)), c) employ preparations swelling in the stomach (balloon tablets) (Agyilirah et al., Int. J. Pharm. 75, 241 (1991)), d) employ preparations having a large spatial expansion (EP-A 235 718) or e) employ bioadhesive preparations which preferably should adhere to the mucous membranes of the gastrointestinal tract (R. Khosla, S. S. Davis, J. Pharm. Pharmacol. 39, 47 (1987)).

Another delayed-release technique makes use of a matrix of hydrophilic polymers and, if appropriate, pharmaceutical excipients in which the active compound is embedded. In an aqueous environment, the polymer swells to give a gel, which then either slowly erodes (together with the poorly soluble active compound) or diffuses through the (readily soluble) active compound. The polymer can by hydrophilic, hydrophobic or mixed hydrophilic/hydrophobic. At present, matrix tablets are very popular, since they are comparatively inexpensive and highly tolerable and can be produced in conventional equipment.

Another method consists in the use of buffered or pH-sensitive coatings which allow controlled release in certain sections of the gastrointestinal tract.

A technically complicated method consists in the use of osmotic systems (OROS) which function according to the following principle: water penetrates slowly into the tablet through a water-permeable membrane and leads to swelling of a water-swellable ingredient there; the pressure resulting due to the increase in volume drives the active compound out of the tablets through an opening intended for this purpose.

All these techniques have disadvantages, in particular expensive and complicated production methods, inter- and intraindividual variability or dependence of the desired action on the posture.

In the production of delayed-release preparations, care also has to be taken in each case of where the absorption of the active compound can take place: the smaller the absorption window, the more difficult the production of delayed-release preparations turns out to be. Quinolones such as ciprofloxacin, for example, are mainly absorbed in the upper part of the small intestine (duodenum); absorption in the lower part of the small intestine and in the large intestine is significantly lower (S. Harder et al., Br. J. Clin. Pharmacol. 30, 35-39, (1990)). Therefore the active compound must be released in order to achieve maximum bioavailability before the preparation leaves this absorption window. Moreover, the strong influence of the pH of the surrounding medium on the solubility of quinolone active compounds has to be taken into account; it decreases with increasing pH.

The object of the invention was therefore to make available delayed-release preparations of quinolone antibiotics which guarantee an adequate therapeutic action on administration once daily.

The invention therefore relates to an orally administrable antibiotic matrix preparation comprising quinolone active compound, characterized in that it releases 80% of the active compound both in 0.1 N hydrochloric acid and in acetate buffer at pH 4.5 in the USP XXIV paddle test at 50 revolutions per minute/37.degree. C. in the course of 1 to 4 hours. In order to prevent floating up of the tablet during the test, it can be placed in a wire cage, as is described, for example, in the Japanese Pharmacopoeia.

The term "quinolone active compound" in the context of the present invention denotes the class consisting of the substances having a quinolone parent structure which can be used as antiinfectives, in particular the quinolonecarboxylic acids. Preferred quinolone active compounds include ciprofloxacin, olamufloxacin, clinafloxacin, trovafloxacin, cadrofloxacin, alatrofloxacin mesylate, gatifloxacin, rufloxacin, sparfloxacin, levofloxacin, irloxacin, grepafloxacin, moxifloxacin, prulifloxacin, pazufloxacin, gemifloxacin, sitafloxacin, tosulfloxacin, amifloxacin, lomefloxacin, R-lomefloxacin and nitrosoxacin-A. The most preferred quinolone active compound is ciprofloxacin and its hydrates.

The term "quinolone active compound" in the context of the present invention also includes quinolone derivatives which only release the active compound in the body ('prodrugs'), e.g. esters of a quinolonecarboxylic acid.

According to a preferred embodiment, the preparation according to the invention contains as active compound a combination, preferably a mixture, of two different quinolone derivatives. An example of such an embodiment according to the invention would be a preparation which as active compound contains a mixture of two different quinolone salts.

A preferred embodiment relates to preparations which as active compound contain the mixture of a free quinolone base and its salt. Mixtures of ciprofloxacin hydrochloride and ciprofloxacin betaine are particularly preferred.

Ciprofloxacin hydrochloride is highly soluble, for example, at low pH values; the solubility is significantly decreased, however, at the pH of the intestinal tract ($\geqq 6.5$). However, it has turned out that mixtures of ciprofloxacin hydrochloride and free ciprofloxacin base (betaine) in a weight ratio of 1:20 to 20:1, in particular 1:10 to 10:1, are released from the preparation largely independently of pH (in the pH range from 1 to 4.5). An equivalent effect can also be achieved by using mixtures of other derivatives, e.g. salts, bases or prodrugs of the active compound. Mixtures of stereoisomers in the context of the invention do not come, however, under the term "combination of two different quinolone derivatives", but rather mixtures of hydrate and anhydrate.

A particular embodiment of the preparations according to the invention relates to matrix tablets. Preferred matrix tablets contain a delayed-release part (CR part) and a rapid-release part (IR part). Suitable release-delaying polymers for the matrix are water-swellable polymers, e.g. polysaccharides such as starches and starch derivatives (maize, wheat, rice and potato starch, carboxymethyl starches, sodium starch glycolates), cellulose ethers such as alkylcelluloses, hydroxyalkylcelluloses, carboxyalkylcelluloses and their alkali metal salts (methyl-, hydroxymethyl-, hydroxyethyl-, hydroxypropyl- and sodium carboxymethylcelluloses, crosslinked carboxymethylcelluloses), dextrins, dextran, pectins, polyoses, gum arabic, tragacanth, carrageenan, galactommanans such as guar gum, algin, alginic acid and alginates, polypeptides and proteins such as gelatin and casein, furthermore chitin derivatives such as chitosan, fully synthetic polymers such as (meth)acrylic acid copolymers (methyl methacrylate, hydroxymethyl methacrylate copolymers, polyvinyl alcohol, uncrosslinked polyvinylpyrrolidone and vinylpyrrolidone copolymers, and mixtures of the compounds mentioned. Since the water-swellable polymers form gels in the presence of water, they can also be called "gel-forming polymers".

Highly viscous polymers are often used for delayed-release preparations. In the present invention, it has been found, however, that low-viscosity polymers positively effect the release behaviour of the preparations. In principle, all hydrophilic polymers of low viscosity can be used for the purpose of delaying release. The term "low viscosity" in the context of the present invention means an (apparent) viscosity of 5 to 400 mPa$^2$s (cP), preferably of at most 75 cP, in particular of at most 50 cP, measured using a rotary viscometer as a 2% strength by weight aqueous solution at 20° C.

Hydroxypropylmethylcellulose (HPMC) is particularly preferred. HPMC of USP XXIV Specification 2910, i.e. having a methoxy content of 28 to 30% by weight and a hydroxypropoxy content of 7 to 12% by weight, e.g. Metolose® 60 SH (Shinetsu, Japan) is especially preferred. The desired degree of delay of the preparation can be adjusted by choice of viscosity and amount of HPMC.

Preferred HPMC has a viscosity of 5 to 400 cP, preferably of at most 75 cP, in particular of at most 50 cP (in each case measured using a rotary viscometer as a 2% strength by weight aqueous solution at 20° C.).

The content of the hydrophilic polymer, preferably of the HPMC, can vary within wide limits. Preferably, however, 1 part by weight of hydrophilic polymer per 2 to 20, preferably per 5 to 15, parts by weight of active compound is employed.

In order to guarantee the release of the active compound from the dose form even in the small intestine and to keep the pH of the external layer and the environment of the preparation in the acidic range and thereby to prevent as largely as possible the risk of the precipitation of the active compound in the higher pH of the intestinal fluid, an organic acid can be incorporated into the preparation (if present, preferably in the delayed-release part); in this way, the active compound is prepared in a form which is more accessible for absorption. For this purpose, preferred organic acids have 2 to 10 C atoms and 1 to 4 carboxyl groups, for example acetic acid, malonic acid, succinic acid, fumaric acid, tartaric acid and citric acid.

Besides active compound, hydrophilic release-delaying polymer and, if appropriate, organic acid, the preparations according to the invention can also contain disintegrants, e.g. crosslinked polyvinylpyrrolidone such as ®Kollidon CL, glidants, e.g. colloidal silica such as ®Aerosil, hydrogenated vegetable oils, stearic acid, talc or mixtures thereof, lubricants, e.g. magnesium stearate, and also, if appropriate, other excipients. Both glidants and lubricants are preferably incorporated into the granules before the tabletting phase.

The tablets can then be coated in order, if appropriate, to mask a bitter taste of the active compound, to protect the active compound from the effect of light and/or in order to make the tablets aesthetically more pleasing. The coating can be carried out, for example, by spraying on an aqueous suspension of: film formers, e.g. HPMC, plasticizers, e.g. polyethylene glycol, and light-scattering and light-absorbing pigments, e.g. titanium dioxide. To dry off the water, hot air can be directed at the tablet bed during the coating.

Delayed-release preparations can be prepared using the components described. Besides the delayed-release part (CR part), a rapid-release part (IR part) can also be employed in order to obtain a rapid influx and a higher plasma level. Rapid-release (IR) preparations are understood in the context of the present invention as meaning those which release the active compound according to USP XXIV paddle method as rapidly as desired, preferably within 3 minutes to less than 60 minutes. The rapid release can be controlled within certain limits by variation of the composition, e.g. by variation of the disintegrant content, or by the production parameters. Rapid-release parts of the preparation according to the invention do not unconditionally have to contain two different quinolone derivatives.

It is thus possible to produce combination preparations which in a single-unit dose form contain preparations having different release profiles: thus preparations having a different release profile can be used in order to control the plasma level exactly timewise. "Combination preparations" within the meaning of the invention are understood as meaning not only single-unit dose forms ('fixed combinations') and combination packs, which separately of one another each contain a preparation having a different release profile (kit of parts), but also IR or CR parts which are administered simultaneously or at different times, provided they are employed for the treatment or prophylaxis of the same disease.

The present invention thus also relates to a combination preparation which has a rapid-release part and a delayed-release part, e.g. in the form of a two-layer tablet. The rapid-release part can contain quinolone active compound (e.g. ciprofloxacin hydrochloride and ciprofloxacin betaine), disintegrant (e.g. crosslinked polyvinylpyrrolidone such as Kollidon®CL), glidants (colloidal silica, e.g. Aerosil ®) and lubricants (e.g. magnesium stearate) and, if appropriate, organic acid or other excipients. The delayed-release parts can contain active compound (ciprofloxacin hydrochloride and ciprofloxacin betaine), the release-delaying polymer (e.g. HPMC of low viscosity), organic acid (e.g. succinic acid), a glidant (e.g. colloidal silica) and a lubricant (e.g. magnesium stearate) and, if appropriate, further excipients. The starting materials for the rapid-release and the delayed-release part can be granulated before tabletting (e.g. using wet or dry granulation techniques). The granules can be mixed with glidants and lubricants, and the compressible (ready-to-compress) granules of the two layers can be tabletted (e.g. with the use of conventional two-layer tabletting machines) to give two-layer tablets. Some of the glidant could also be granulated.

Since the addition of an organic acid increases the release rate of the active compound, in particular of ciprofloxacin hydrochloride and betaine, it may also be recommended to admix organic acid to the IR part.

The delayed-release preparations according to the invention expediently contain 500 to 1000 mg of active compound, calculated as betaine, per single-unit dose form. "Single-unit dose forms" are understood as meaning those preparations which are administered as an individual dose, e.g. tablets, coated tablets or capsules.

For the production of delayed-release preparations according to the invention having an IR and CR part, it is possible to use, for example, the following process: for the production of the IR part the active compound (preferably as a mixture of two derivatives) is mixed with disintegrant, in particular Kollidon CL, and granulated and mixed with glidant, in particular aerosol, and lubricant, in particular magnesium stearate, in order to obtain compactable (ready-to-compress) IR granules.

For the delayed-release part, the active compound (as a mixture of two derivatives) is mixed with acid, e.g. succinic acid, and gel-forming polymer, in particular HPMC, and granulated. These CR granules are mixed with glidant, in particular Aerosil ®, and lubricant, in particular magnesium stearate, in order to obtain compressible (ready-to-compress) CR granules. The (ready-to-compress) CR granules and the IR granules are tabletted using a conventional two-layer tabletting machine to give a two-layer tablet. The tablet obtained can then be coated.

The following working examples are intended to explain the subject of the invention with the aid of two-layer tablets, but without restricting it thereto.

EXAMPLES

Example 1

| Amount in mg | Substances employed |
| --- | --- |
| 366.70 | Ciprofloxacin hydrochloride |
| 41.70 | Ciprofloxacin betaine |
| 46.700 | Kollidon CL** |
| 4.30 | Aerosil 200*** |
| 4.70 | Magnesium stearate |
| 464.10 | Subtotal IR part |
| 302.70 | Ciprofloxacin hydrochloride |
| 464.30 | Ciprofloxacin betaine |
| 125.40 | Succinic acid |
| 103.10 | Hydroxypropylmethylcellulose 50 cP* |
| 5.20 | Aerosil 200*** |
| 9.30 | Magnesium stearate |
| 1010.00 | Subtotal CR part |
| 18.00 | Hydroxypropylmethylcellulose 15 cP* |
| 6.00 | Titanium dioxide |
| 6.00 | Polyethylene glycol 400**** |
| 30.00 | Coating sub-total |
| 23 × 9.5 mm | Oblong tablet |

*Viscosity, in each case measured as a 2% strength by weight aqueous solution at 20° C.
**Crosslinked polyvinylpyrrolidone
***Colloidal silica, specific surface area 200 m$^2$/g
****The numerical information relates to the average molecular weight Example 2

| Amount in mg | Substances employed |
| --- | --- |
| 183.40 | Ciprofloxacin hydrochloride |
| 20.90 | Ciprofloxacin betaine |
| 22.30 | Kollidon CL |
| 2.30 | Magnesium stearate |
| 1.10 | Aerosil 200 |
| 230.00 | Subtotal IR part |
| 151.40 | Ciprofloxacin hydrochloride |
| 232.10 | Ciprofloxacin betaine |
| 64.00 | Succinic acid |
| 52.30 | Hydroxypropylmethylcellulose 15 cP |
| 7.60 | Magnesium stearate |
| 2.60 | Aerosil 200 |
| 510.00 | Subtotal CR part |
| 12.00 | Hydroxypropylmethylcellulose 15 cP |
| 4.00 | Polyethylene glycol 400 |
| 4.00 | Titanium dioxide |
| 20.00 | Coating sub-total |
| 19 × 8 mm | Oblong tablet |

Example 3

| Amount in mg | Substances employed |
| --- | --- |
| 183.40 | Ciprofloxacin hydrochloride |
| 20.90 | Ciprofloxacin betaine |
| 22.30 | Kollidon CL |
| 2.30 | Magnesium stearate |
| 1.10 | Aerosil 200 |
| 230.00 | Subtotal IR part |
| 151.40 | Ciprofloxacin hydrochloride |
| 232.10 | Ciprofloxacin betaine |
| 65.10 | Succinic acid |
| 73.00 | Hydroxypropylmethylcellulose 15 cP |
| 10.70 | Magnesium stearate |
| 2.70 | Aerosil 200 |
| 535.00 | Subtotal CR part |
| 12.00 | Hydroxypropylmethylcellulose 15 cP |
| 4.00 | Polyethylene glycol 3350 |
| 4.00 | Titanium dioxide |
| 20.00 | Coating sub-total |
| 19 × 8 mm | Oblong tablet |

Example 4

| Amount in mg | Substances employed |
|---|---|
| 183.40 | Ciprofloxacin hydrochloride |
| 20.90 | Ciprofloxacin betaine |
| 22.30 | Kollidon CL |
| 2.30 | Magnesium stearate |
| 1.10 | Aerosil 200 |
| 230.00 | Subtotal IR part |
| 151.40 | Ciprofloxacin hydrochloride |
| 232.10 | Ciprofloxacin betaine |
| 64.00 | Succinic acid |
| 72.00 | Hydroxypropylmethylcellulose 50 cP |
| 7.90 | Magnesium stearate |
| 2.60 | Aerosil 200 |
| 530.00 | Subtotal CR part |
| 12.00 | Hydroxypropylmethylcellulose 15 cP |
| 4.00 | Polyethylene glycol 400 |
| 4.00 | Titanium dioxide |
| 20.00 | Coating sub-total |
| 19 × 8 mm | Oblong tablet |

Example 5

| Amount in mg | Substances employed |
|---|---|
| 262.00 | Ciprofloxacin hydrochloride |
| 29.80 | Ciprofloxacin betaine |
| 8.90 | Succinic acid |
| 42.20 | Kollidon CL |
| 1.80 | Aerosil 200 |
| 5.30 | Magnesium stearate |
| 350.00 | Subtotal IR part |
| 116.40 | Ciprofloxacin hydrochloride |
| 178.50 | Ciprofloxacin betaine |
| 134.00 | Succinic acid |
| 87.80 | Hydroxypropylmethylcellulose 15 cP |
| 2.70 | Aerosil 200 |
| 10.60 | Magnesium stearate |
| 530.00 | Subtotal CR part |
| 12.00 | Hydroxypropylmethylcellulose 15 cP |
| 4.00 | Polyethylene glycol 400 |
| 4.00 | Titanium dioxide |
| 20.00 | Coating sub-total |
| 19 × 8 mm | Oblong tablet |

Example 6

| Amount in mg | Substances employed |
|---|---|
| 183.40 | Ciprofloxacin hydrochloride |
| 20.90 | Ciprofloxacin betaine |
| 6.20 | Succinic acid |
| 24.70 | Kollidon CL |
| 1.20 | Aerosil 200 |
| 3.60 | Magnesium stearate |
| 240.00 | Subtotal IR part |
| 151.40 | Ciprofloxacin hydrochloride |
| 232.10 | Ciprofloxacin betaine |
| 174.00 | Succinic acid |
| 95.70 | Hydroxypropylmethylcellulose 15 cP |
| 3.40 | Aerosil 200 |
| 13.40 | Magnesium stearate |
| 670.00 | Subtotal CR part |
| 12.00 | Hydroxypropylmethylcellulose 15 cP |
| 4.00 | Polyethylene glycol 400 |
| 4.00 | Titanium dioxide |
| 20.00 | Coating sub-total |
| 19 × 8 mm | Oblong tablet |

Example 7

| Amount in mg | Substances employed |
|---|---|
| 366.70 | Ciprofloxacin hydrochloride |
| 41.70 | Ciprofloxacin betaine |
| 46.60 | Kollidon CL |
| 4.70 | Magnesium stearate |
| 2.30 | Aerosil 200 |
| 462.00 | Subtotal IR part |
| 302.70 | Ciprofloxacin hydrochloride |
| 464.30 | Ciprofloxacin betaine |
| 125.30 | Succinic acid |
| 103.00 | Hydroxypropylmethylcellulose 15 cP |
| 20.50 | Magnesium stearate |
| 5.20 | Aerosil 200 |
| 1021.00 | Subtotal CR part |
| 18.00 | Hydroxypropylmethylcellulose 15 cP |
| 6.00 | Polyethylene glycol 3350 |
| 6.00 | Titanium dioxide |
| 30.00 | Coating sub-total |
| 23 × 9.5 mm | Oblong tablet |

Comparative Example A

| Amount in mg | Substances employed |
|---|---|
| 357.00 | Ciprofloxacin betaine |
| 58.00 | Kollidon CL |
| 6.00 | Magnesium stearate |
| 4.00 | Aerosil 200 |
| 425.00 | Subtotal IR part |
| 833.00 | Ciprofloxacin betaine |
| 108.00 | Succinic acid |
| 108.00 | Hydroxypropylmethylcellulose 50 cP |
| 16.00 | Magnesium stearate |
| 10.00 | Aerosil 200 |
| 1075.00 | Subtotal CR part |
| 18.00 | Hydroxypropylmethylcellulose 15 cP |
| 6.00 | Polyethylene glycol 400 |
| 6.00 | Titanium dioxide |
| 30.00 | Coating sub-total |
| 23 × 9.5 mm | Oblong tablet |

Comparative Example B

| Amount in mg | Substances employed |
| --- | --- |
| 357.00 | Ciprofloxacin betaine |
| 58.00 | Kollidon CL |
| 6.00 | Magnesium stearate |
| 4.00 | Aerosil 200 |
| 425.00 | Subtotal IR part |
| 833.00 | Ciprofloxacin betaine |
| 108.00 | Succinic acid |
| 108.00 | Hydroxypropylmethylcellulose 3 cP |
| 16.00 | Magnesium stearate |
| 10.00 | Aerosil 200 |
| 1075.00 | Subtotal CR part |
| 18.00 | Hydroxypropylmethylcellulose 15 cP |
| 6.00 | Polyethylene glycol 400 |
| 6.00 | Titanium dioxide |
| 30.00 | Coating sub-total |
| 23 × 9.5 mm | Oblong tablet |

In 0.1N HCl solution or acetate buffer at pH 4.5, the preparations according to the invention of Examples 1 to 7 show largely pH-independent release in conventional release apparatuses (USP paddle test), while the preparations of Comparative Examples A and B show strong pH dependence.

We claim:

1. A process for the production of an orally administrable antibiotic matrix preparation comprising a mixture of a salt with the free base of a quinolone active compound at a salt-to-free base weight ratio of from 1:10 to 10:1, wherein the preparation releases 80% of the active compound both in 0.1 N hydrochloric acid and in acetate buffer at pH 4.5 in the USP XXIV paddle test at 50 revolutions per minute/37° C. in the course of 1 to 4 hours, and wherein the preparation is a combination preparation comprising a rapid-release (IR) part and a delayed release (CR) part, according to which one part of the active compound is mixed with disintegrant, granulated and mixed with glidant and lubricant (IR part), and another part of the active compound is mixed with acid and a gel-forming polymer, granulated and mixed with glidant and lubricant (CR part), and IR part and CR part are tabletted to give combination tablets and the resulting tablets are coated.

2. The process of claim 1, wherein the salt-to-free base weight ratio is from about 1.3:1 to about 1.8:1.

3. The process of claim 1, wherein the quinolone active compound is ciprofloxacin.

4. The process of claim 3, wherein the salt and free base are ciprofloxacin hydrochloride and ciprofloxacin betaine, respectively.

5. The process of claim 1, wherein the gel-forming polymer is selected from the group consisting of alkylcellulose, hydroxyalkylcellulose, and carboxyalkylcellulose and its alkali metal salts.

6. The process of claim 5, wherein the gel-forming polymer is a hydroxyalkylcellulose.

7. The process of claim 5, wherein the gel-forming polymer is a crosslinked carboxymethylcellulose or an alkali metal salt thereof.

8. The process of claim 6, wherein the gel-forming polymer is hydroxypropylmethylcellulose of a viscosity of at most 75 cP, measured as a 2% strength by weight aqueous solution at 20° C.

9. The process of claim 8, wherein the hydroxypropylmethylcellulose has a viscosity of at most 50 cP, measured as a 2% strength by weight aqueous solution at 20° C.

10. The process of claim 1, wherein the acid is an organic acid having from 2 to 10 carbon atoms and from 1 to 4 carboxyl groups.

11. The process of claim 10, wherein the organic acid is selected from the group consisting of acetic acid, malonic acid, succinic acid, fumaric acid, tartaric acid and citric acid.

12. The process of claim 10, wherein the organic acid is succinic acid.

* * * * *